United States Patent
Kadir et al.

(10) Patent No.: US 11,704,792 B2
(45) Date of Patent: Jul. 18, 2023

(54) SYSTEM, METHOD AND APPARATUS FOR ASSISTING A DETERMINATION OF MEDICAL IMAGES

(71) Applicants: Optellum Limited, Oxford (GB); Timor Kadir, Oxford (GB); Lyndsey Pickup, Oxford (GB); Vaclav Potesil, Oxford (GB); Jerome Declerck, Oxford (GB)

(72) Inventors: Timor Kadir, Oxford (GB); Lyndsey Pickup, Oxford (GB); Vaclav Potesil, Oxford (GB); Jerome Declerck, Oxford (GB)

(73) Assignee: Optellum Limited, Oxford (GB)

( * ) Notice: Subject to any disclaimer, the term of this patent is extended or adjusted under 35 U.S.C. 154(b) by 0 days.

(21) Appl. No.: 16/645,872

(22) PCT Filed: Sep. 24, 2018

(86) PCT No.: PCT/EP2018/075794
§ 371 (c)(1),
(2) Date: Mar. 10, 2020

(87) PCT Pub. No.: WO2019/057967
PCT Pub. Date: Mar. 28, 2019

(65) Prior Publication Data
US 2020/0279369 A1   Sep. 3, 2020

(30) Foreign Application Priority Data
Sep. 22, 2017   (GB) .................................... 1715331

(51) Int. Cl.
*G06K 9/00*   (2022.01)
*G06T 7/00*   (2017.01)
(Continued)

(52) U.S. Cl.
CPC .......... *G06T 7/0012* (2013.01); *G16H 30/40* (2018.01); *G16H 50/20* (2018.01); *G16H 50/30* (2018.01);
(Continued)

(58) Field of Classification Search
None
See application file for complete search history.

(56) References Cited

U.S. PATENT DOCUMENTS

2015/0213302 A1 *   7/2015   Madabhushi ...... G06K 9/00147
                                                              382/133
2016/0196647 A1 *   7/2016   Madabhushi .... G01R 33/34084
                                                              382/131

(Continued)

OTHER PUBLICATIONS

EPO Article 94 Communication; EPO S/N 18 778 878.1-1126; dated Nov. 2, 2021.

*Primary Examiner* — Wei Wen Yang
(74) *Attorney, Agent, or Firm* — Optimus Patents US, LLC

(57) ABSTRACT

A Computer Aided Diagnosis, CADx, system (200) is described that comprises: at least one input (210, 212, 214) configured to provide at least one input medical image; and a CADx processing engine (220) configured to receive and process the at least one input medical image and produce at least one CADx score. A CADx score mapping circuit is operably coupled to the CADx processing engine (220) and configured to: map the at least one CADx score to a risk adjusted virtual score; and generate an output (235) of at least the risk adjusted virtual score associated with the processed at least one input medical image. The at least one CADx score and the risk adjusted virtual score correspond to an equivalent risk of condition or disease associated with a patient.

18 Claims, 10 Drawing Sheets

(51) Int. Cl.
*G16H 50/30* (2018.01)
*G16H 50/70* (2018.01)
*G16H 50/20* (2018.01)
*G16H 30/40* (2018.01)

(52) U.S. Cl.
CPC ... *G16H 50/70* (2018.01); *G06T 2207/10081* (2013.01); *G06T 2207/10104* (2013.01); *G06T 2207/20081* (2013.01); *G06T 2207/20084* (2013.01); *G06T 2207/30064* (2013.01)

(56) References Cited

U.S. PATENT DOCUMENTS

| | | |
|---|---|---|
| 2016/0253466 A1 | 9/2016 | Agaion |
| 2017/0061087 A1* | 3/2017 | Boroczky ......... G06F 16/24578 |
| 2018/0012356 A1* | 1/2018 | Madabhushi ........ G06K 9/6267 |

* cited by examiner

FIG. 1 – Prior Art

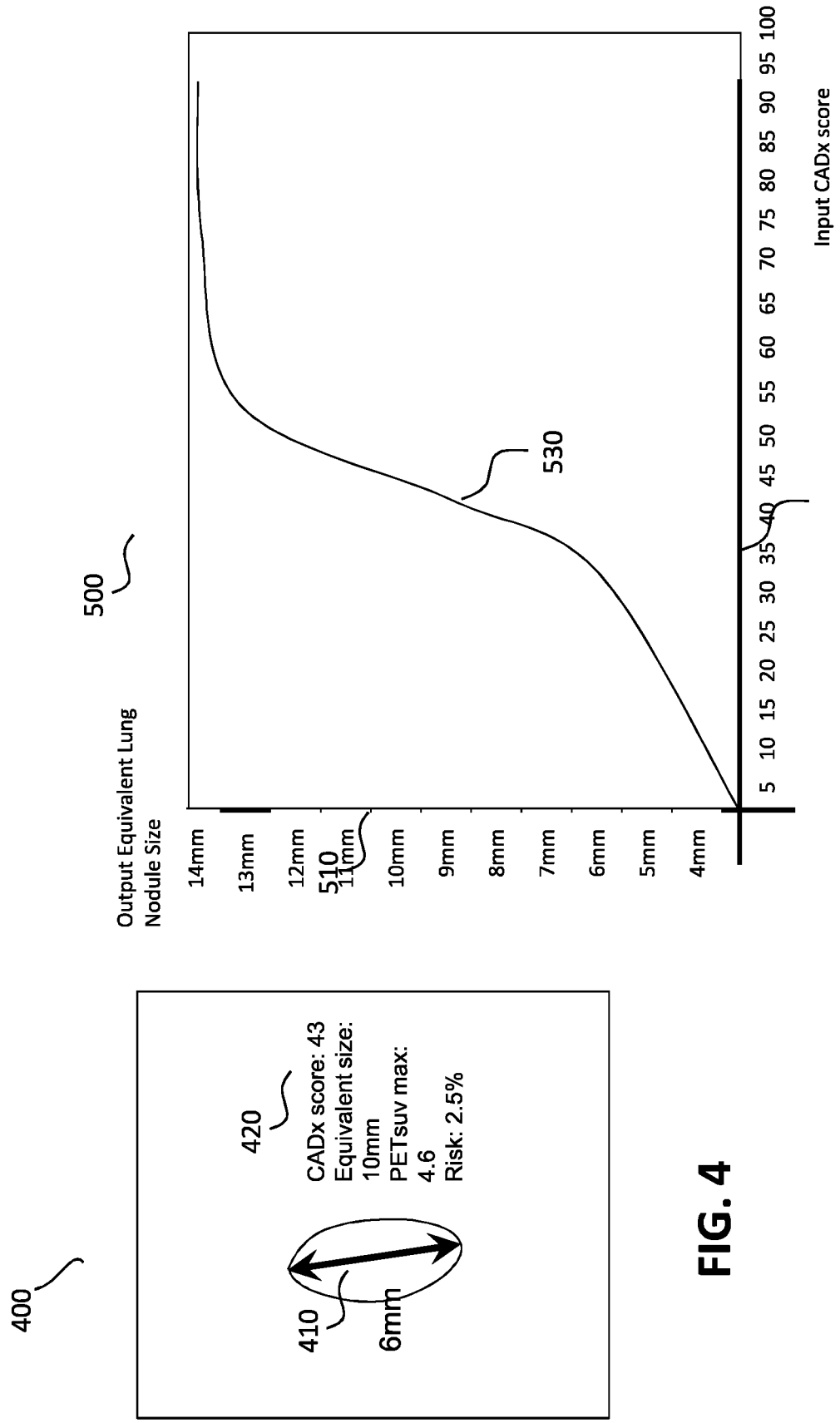

SYSTEM, METHOD AND APPARATUS FOR ASSISTING A DETERMINATION OF MEDICAL IMAGES

FIELD OF THE INVENTION

This invention relates to the field of Computer Aided Diagnosis (CADx) systems and methods for assisting determination of medical images, used to support clinicians in healthcare. In particular, the field relates to risk Computer Aided Diagnosis systems to assist the reading and reporting of medical images by radiologists and the interpretation of the radiologist's report by the physician responsible for patient care.

BACKGROUND OF THE INVENTION

In the field of medical imaging, a variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an 'imaging modality'.

Typically, a scan provides a 'dataset'. The dataset comprises digital information about the value of a variable at each of many spatial locations in either a two-dimensional or (more typically) a three-dimensional space. As a specific example, a CT scan may provide images of the chest of a patient. Such a CT scan might, as a more specific example, show lung nodules in the chest.

Computer Aided Detection (CADe) systems are also known aim to assist clinicians. CADe systems aim to provide a clinician with standardised, objective and repeatable information. That information might typically relate to structures, both normal and lesions, in a person. Examples of CADe systems include the mammography CADe systems available commercially such as 'PowerLook Advanced Mammography Platform' from 'iCAD' and the 'Image-Checker' from 'Hologic'. The purpose of such products is to reduce the number of findings missed by a radiologist. These products attempt to achieve this by detecting suspicious regions in the image and showing these to the radiologist.

CADe systems may be used as a so-called 'Second Reader' system. This phrase is based on an approach whereby a radiologist first looks at an image resulting from a scan, for example a mammogram. The radiologist will then, based on training and experience, identify areas of the scan where the radiologist considers that there may need to be further investigation, for example a biopsy. However, the radiologist can then consider the CADe findings. Those findings might involve a display to highlight any additional suspicious regions on the mammogram. The radiologist will then, based on training and experience, look at those further areas of the scan. The CADe system is thereby, figuratively speaking, performing a second look at the scan. The results of that second look at the scan may be that the radiologist will be directed to areas of the scan that he/she had overlooked. In this way, CADe systems are designed to reduce 'false negatives', which are also termed 'missed findings'. Thus CADe systems perform a support role to clinicians.

Computer Aided Diagnosis (CADx) systems are a related technology to CADe. CADx systems attempt to solve a different problem, and relate generally to risk assessment. Instead of focussing on potentially missed findings as in CADe, they try to assist the user to classify findings correctly, either as malignant or benign in the case of cancer. They rely on the user to detect, namely identify, abnormalities, but then typically provide a score that is indicative of risk of malignancy. There are many examples of such CADx systems proposed within the academic literature. However, fewer systems are available commercially, and hence used in clinical practice.

This discrepancy is indicative of the difficulties in deploying practical systems with the known approaches. The output of known CADx systems is typically some kind of score. That score indicates the risk or likelihood of disease, or its absence. An example of a commercial CADx system is the 'Transpara' product from 'Screenpoint'. There are many non-clinical CADx systems in the academic literature.

However, such known techniques have the disadvantage that the output of the system, which, as described above, is, at best, a number that indicates the confidence the system has in its decision and is consequently very difficult to interpret by the physician and incorporate into their decision making. The reason is that clinicians need to adjust or calibrate their judgement to the output of the system and to incorporate it with all the other factors that they need to take into account in clinical decision making. This judgement adjustment can take a long time to make for the medical field as a whole, such as within a single institution and/or for an individual. Partly, this is an issue of trust and confidence in the system and partly it's an issue of training. Nevertheless, this is one of the main reasons why such systems face significant barriers to adoption in a practical context and consequently take-up is very slow. Moreover, the adoption of such systems requires a clinical validation that is deemed acceptable to clinical users. To this end, the data for training and validation should be sufficiently comparable to that encountered by the clinician in their institution.

The problem is exacerbated when the CADx system is to be updated with an improved performance. Since many such systems are built using machine learning technology, any improvement in the performance of the system, or even a significant change in the way in which scores are produced without an improvement in performance, will require that the clinician re-adapts their decision making. For example, a change to the training data will result in different scores for the same input image.

FIG. 1 illustrates a block diagram 110 of a conventional CADx system 120 that takes one or more input datasets of, say, medical images 110, 112, 114. The CADx system 120 produces a score 125 as an indicator of the system's confidence of whether (or not) the dataset exhibits disease. This score is then interpreted by the radiologist or a physician at 130, with other clinical parameters, during a decision making process. However, in known systems, the output score 125 of the CADx system 120, for a particular input dataset, does not conform to any accepted clinical scale. This makes decisions from the output score 125 to be somewhat variable across a wide range of readers. Furthermore, the output score 125 will change with new training data or a change in parameters.

One conventional solution is to provide the reader 130 with a threshold that they can apply to the CADx output score 125. For instance, output scores 125 above this threshold should be considered indicative of disease, and those below the threshold should not. This approach is analogous to that used for other medical tests such as measuring the level of cholesterol in the blood as an indicator of heart disease risk, where certain thresholds are used to stratify patients into low, medium and high risk. Similarly, numerous schemes have been devised to standardise the reading and reporting of findings in Breast (BIRADS) and Lung imaging (LungRADS), which use thresholds agreed by clinical experts to stratify patient risk.

However, even though such a solution is conventional in the field, it still has the disadvantage that the experts and clinicians in the field need to understand and agree the thresholds used. This can take a long time and presents a significant barrier to building trust in the system and for the system to gain adoption in a practical context. Moreover, the results can result in some variability in interpretation where different clinical centres adopt different thresholds, which may be determined by other factors particular to the patient population under study.

The document by Sun T, Zhang R, Wang J, Li X, Guo X (2013) titled 'Computer-Aided Diagnosis for Early-Stage Lung Cancer Based on Longitudinal and Balanced Data', PLoS ONE 8(5): e63559. doi:10.1371/journal.pone.0063559 describes a system that is designed to produce an output between −1 and 1. For example, see the section 'Methods, sub-section Prediction Model 'where $Y_1 \in \{+1, -1\}$ is the corresponding desired output'.

The document by Way T, Chan H-P, Hadjiiski L, et al. titled 'Computer-Aided Diagnosis of Lung Nodules on CT Scans: ROC Study of Its Effect on Radiologists' Performance Academic radiology. 2010; 17(3):323-332. doi: 10.1016/j.acra.2009.10.016 describes a system produces an output between '1' and '10', as described in the section Methods and Materials, the last paragraph in CAD System, 'The original bin value was mapped linearly as a relative malignancy rating on a scale of '1' to '10''.

Finally, at times, there is a need to update the CADx system when new training and validation data is made available. Based thereon, the output scores can change and require that a new threshold is studied, validated and accepted.

In the document 'New response evaluation criteria in solid tumours: Revised RECIST guideline (version 1.1)', authored by E. A. Eisenhauer et al., and published in the EUROPEAN JOURNAL OF CANCER 45 (2009) 228-247, the authors utilize size in order to measure response to cancer therapy or progression of disease. In Positron Emission Tomography (PET), the reporting radiologist often measures and includes the tracer uptake, i.e. the amount of radiotracer that has accumulated in a particular part of the image, as part of their report. This is conventionally measured using a Standardised Uptake Value (SUV).

Thus, there exists a desire for an improved Computer Aided Diagnosis (CADx) system to facilitate use and clinical deployment of CADx systems, namely the understanding and rapid incorporation of CADx outputs into clinical management of patients.

SUMMARY OF THE INVENTION

Accordingly, the invention seeks to mitigate, alleviate or eliminate one or more of the abovementioned disadvantages singly or in any combination.

According to a first aspect of the present invention, there is provided a CADx system and according to a second aspect of the present invention, there is provided a method of mapping a determined raw CADx score. The CADx system includes at least one input configured to provide at least one input medical image; a CADx processing engine configured to receive and process the at least one input medical image and produce at least one CADx score; and a CADx score mapping circuit operably coupled to the CADx processing engine and configured to map the at least one CADx score to a risk adjusted virtual score; and generate an output of at least the risk adjusted virtual score associated with the processed at least one input medical image; wherein the at least one CADx score and the risk adjusted virtual score correspond to an equivalent risk of condition or disease associated with a patient.

In this manner, the mapping of the at least one CADx score to a risk adjusted virtual score; and generation of an output of at least the risk adjusted virtual score associated with the processed at least one input medical image, where the at least one CADx score and the risk adjusted virtual score correspond to an equivalent risk of condition or disease associated with a patient, may significantly improve the understanding and rapid incorporation of CADx outputs into clinical management of patients.

According to an optional example, the CADx score mapping circuit may be configured to map the at least one CADx score to a risk adjusted virtual score on a clinically accepted scale. In this manner, the output of the CADx system can be more rapidly accepted into and readily utilized in clinical management of patients.

According to an optional example, the CADx score mapping circuit may be configured to analyse a first set of input medical image data to obtain a first score that indicates a value associated with at least one patient having the disease or condition; and apply thereafter a mapping function to the first score based on at least a second set of input medical image data to generate the output of at least the risk adjusted virtual score. In this manner, the CADx system may incorporate information from multiple sources, thereby resulting in an improved classification of disease.

According to an optional example, the first score may be at least one risk adjusted virtual score of at least one second score type having an equivalent risk to the first score, where the at least one second score type comprises at least one of: a modified risk indication; multiple virtual scores of multiple score types; an equivalent Positron Emission Tomography, PET, standardised uptake value, SUV. In this manner, the CADx system may produce an output that is readily interpretable by the clinical user, for example because the clinician is already familiar with the score type of the output.

According to an optional example, the CADx score mapping circuit may be configured to convert the first score type to the at least one risk adjusted virtual score of the at least one second score type using at least one of: an equivalent doubling time factor, an equivalent nodule size. In this manner, the CADx system output can be interpreted by clinicians that are familiar with these measurements, for example in the context of cancer and in particular lung cancer.

According to an optional example, the at least one medical image may include a chest-computed tomography, CT, scan that shows at least one pulmonary nodule. In this manner, the CADx system may be utilized in the context of the management of patients with pulmonary nodules.

According to an optional example, a PET CT scan of a patient may be performed and a measured PET SUV output provide an input indication to the CADx system as to whether or not a nodule is malignant or benign, and the risk adjusted virtual score may indicate a likelihood of nodule malignancy. In this manner, the CADx system may integrate information from PET/CT scans in order to produce an overall likelihood of malignancy.

According to an optional example, the measured PET SUV output may be output either directly or may be first mapped to a virtual PET SUV score that is output. In this manner, the CADx system may utilize either the original or risk adjusted PET SUV score.

According to an optional example, the at least one medical image may include both the at least one medical image and training data that comprises at least one of: meta data, historical data. In this manner, the invention may utilize multiple sources of information when mapping to the risk adjusted virtual score.

According to an optional example, the CADx score mapping circuit may be configured to exhibit monotonic properties that enable the output to include at least the risk adjusted virtual score associated with the processed at least one input medical image and the at least one CADx score. In this manner, the order and smoothness of the CADx score may be maintained in the risk adjusted virtual score.

According to an optional example, the CADx score mapping circuit may be configured to perform at least one from a group of: use a Support Vector Machine for classification of mapping between the at least one CADx score and the risk adjusted virtual score; include factoring in a mapping operation from at least one from a group of: user-specific preferences, more data associated with the patient. In this manner, the CADx may account for user-specific preferences, for example in the manner in which the risk adapted virtual score is calculated.

According to the second aspect of the present invention, there is provided a method of mapping a determined raw CADx score that includes receiving and processing at least one input medical image by a CADx processing engine; producing at least one CADx score; mapping the at least one CADx score to a risk adjusted virtual score, wherein the at least one CADx score and the risk adjusted virtual score correspond to an equivalent risk of condition or disease associated with a patient; and generating an output of at least the risk adjusted virtual score associated with the processed at least one input medical image.

According to an optional example, the method may further include identifying a range of possible values of a first non-modified score; allocating the first non-modified score into one of a plurality of sub-ranges, dependent upon a determined risk of condition or disease for each of the plurality of sub-ranges; and repeating the steps of separating and working for the virtual score, and deriving a mapping function that maps values of the first score to an equivalent risk of the virtual score. In this manner, the non-modified score may be mapped to the risk adapted virtual score across the range of value of the scores.

According to a third aspect of the present invention, there is provided a CADx, system that includes at least one input configured to receive at least one input medical image of a patient; and a CADx processing engine that includes a regressor circuit configured to process the received at least one input medical image; wherein the regressor circuit is trained to generate a risk adjusted virtual score associated with the processed at least one input medical image and wherein the risk adjusted virtual score corresponds to an equivalent risk of condition or disease associated with the patient. In this manner, through the use of a built-in regressor circuit, the CADx system may be trained to directly output the risk adjusted virtual score without a need for a second mapping circuit.

According to an optional example, the regressor circuit may be configured to receive a training dataset and set a target value for each case in the training dataset that corresponds to an equivalent risk of the patient having the condition or disease. In this manner, the regressor circuit may be trained to produce the desired risk adapted virtual score, since for each case in the training set there is a target risk value.

According to an optional example, the regressor circuit may be configured to perform a polynomial or spline regression or a piecewise function to perform the mapping between the at least one CADx score and one or more equivalent value(s) on a clinically accepted scale. In this manner, the mapping function may be fitted between the CADx score and the risk adapted virtual score, which is on a clinically accepted scale in a computationally efficient manner.

According to an optional example, the regressor circuit may employ at least one from a group of: a Random Forest, Support Vector Machine, a Convolutional Neural Network. In this manner, the CADx system may utilize an optimal regression method for the application of interest and available amount of training data.

According to a fourth aspect of the present invention, there is provided a method of mapping a determined raw Computer Aided Diagnosis, CADx, score in a CADx system. The method includes: receiving and processing a plurality of input medical training images by a CADx processing engine; allocating a score for each of the plurality of input medical training images, where the score comprises a range from a first score indicative of disease to a second score indicative of no disease; iteratively training a regressor circuit coupled to the CADx processing engine to predict the score; and generating a risk adjusted virtual score associated with each processed at least one input medical image, wherein the risk adjusted virtual score corresponds to an equivalent risk of condition or disease associated with a patient.

According to an optional example, training a regressor circuit may include performing an iterative regression process on a mapping dataset; and generating a CADx score for each case in the mapping dataset. In this manner, the CADx system may improve its mapping between the CADx score and the risk adjusted virtual score at each iteration.

According to an optional example, training a regressor circuit may include defining and allocating ranges of the score to the mapped dataset. In this manner, the risk or probability of disease may be estimated in each range of the score.

According to an optional example, training a regressor circuit may further include estimating a risk of a condition or disease associated with each input medical training image within a training population or measured on the mapping dataset; generating a risk adjusted virtual score associated with the respective input medical training image; and repeating a regression training operation until convergence is reached. In this manner, the CADx system may be trained to produce a risk adjusted virtual score in an optimal manner and even in the absence of a-priori knowledge of the mapping between the CADx score and the risk adjusted virtual score.

According to a fifth aspect of the present invention, there is provided a Computer Aided Diagnosis, CADx, system that includes at least one input configured to provide at least one input medical image; and a CADx processing engine configured to receive and process the at least one input medical image and produce at least one risk adjusted virtual score. In this manner, the CADx system may produce an output virtual score on a clinical accepted scale, which may be more readily accepted into clinical practice.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 4 illustrates an example of a mapping of the raw CADx data to an equivalent size, equivalent PET SUV maximum value and associated risk, according to examples of the present invention.

FIG. 5 illustrates a graphical mapping function example, including mapping raw CADx scores to an equivalent size, according to examples of the present invention.

DETAILED DESCRIPTION

Examples of the invention solve one or more of the aforementioned problems by mapping a determined raw CADx score to a score that is already accepted by the medical community.

For example, in the case of LungRADS, a size of a lung lesion is a key determining factor in patient stratification. In this scenario, therefore, examples of the invention map the raw CADx score to produce an 'equivalent lesion size'. For example, a lesion may be equivalent to a much bigger lesion because of the particular imaging characteristics that the CADx system considers to be indicative of high risk of malignancy.

RECIST is a standardised quantitative method for measuring and reporting the response to therapy in solid tumours. Hence, in some examples, RECIST may be used to identify a change in lesion size. Thus, in other examples of the invention, the CADx system is configured to produce an 'equivalent lesion size reduction' score so that readers and managing physicians who are familiar with RECIST response assessment can readily understand and interpret the CADx score.

In other examples of the invention, the raw CADx score may be mapped to a virtual or equivalent PET SUV, so that readers and managing physicians who are familiar with SUV can readily understand and interpret the CADx score.

Thus, examples of the invention modify the output of the CADx system to produce an output of a risk adjusted virtual score that the reading physician is familiar with, e.g. a clinically accepted score. Examples of the modified output in a format that the reading physician is familiar with, may include:

1) Lesion single or bidirectional size in CT or MRI;
2) Tumour doubling time in CT or MRI;
3) Contrast enhancement in CT or MRI;
4) PET uptake in FDG PET or PET/CT;
5) MRI Apparent Diffusion Coefficient (ADC).

The above five format options are all examples from the imaging field. However, the CADx system according to some examples of the invention is able to create an equivalent score for other clinical measurements, such as a Prostate Specific Antibody (PSA) level or Cholesterol blood level.

Figure 2:
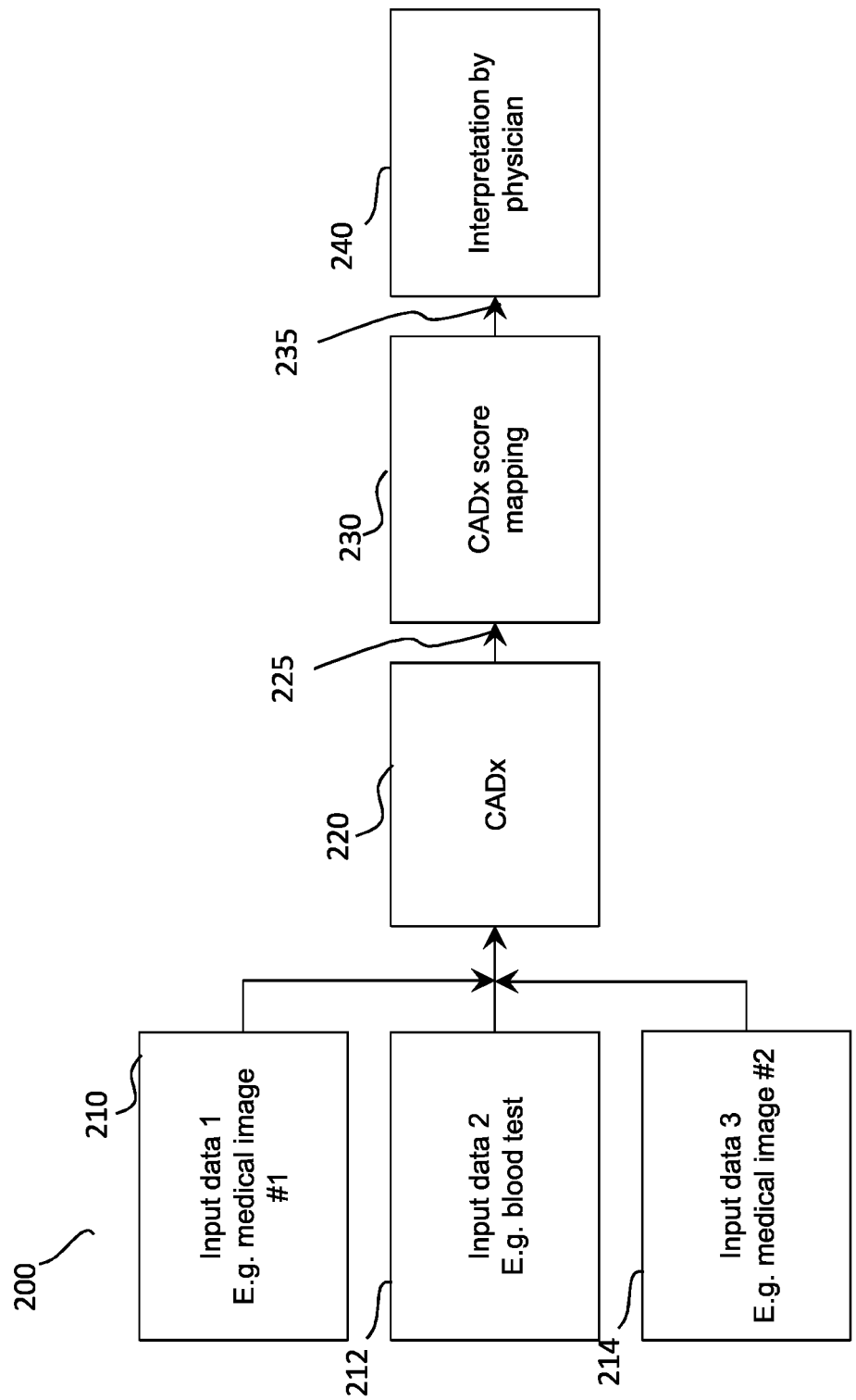
FIG. 2 illustrates a simplified implementation of a CADx system, in hardware, firmware or software or any combination thereof, configured to map a raw CADx score to a scale that is already clinically accepted, according to examples of the present invention.

Referring now to FIG. 2, a simplified implementation 200 of a CADx system configured to map a raw CADx score to a scale that is already clinically accepted is illustrated, according to examples of the present invention. The CADx system 200 takes a number of inputs, in the example illustrated Data 1 is a medical image 210, Data 2 is a result of a blood test 212 and Data 3 is another medical image 214 (for example of another modality or taken at another time to Data 1). A CADx processing engine 220 takes such inputs and either automatically, or with some user-input, produces a score 225 that, say, indicates a risk of the condition or disease. For the purposes of illustration, let us assume that the output is a real number between '0' and '99', indicating the predicted absence or presence of the condition or disease respectively. In accordance with examples of the invention, this score 225 is then modified in CADx score mapping circuit 230, which may be implemented using logic gates in firmware in some example implementations. At least one (modified) risk adjusted virtual score 235, output from the CADx score mapping circuit may then be interpreted by the radiologist or a physician at 240, with other clinical parameters, during a decision making process.

Figure 3:
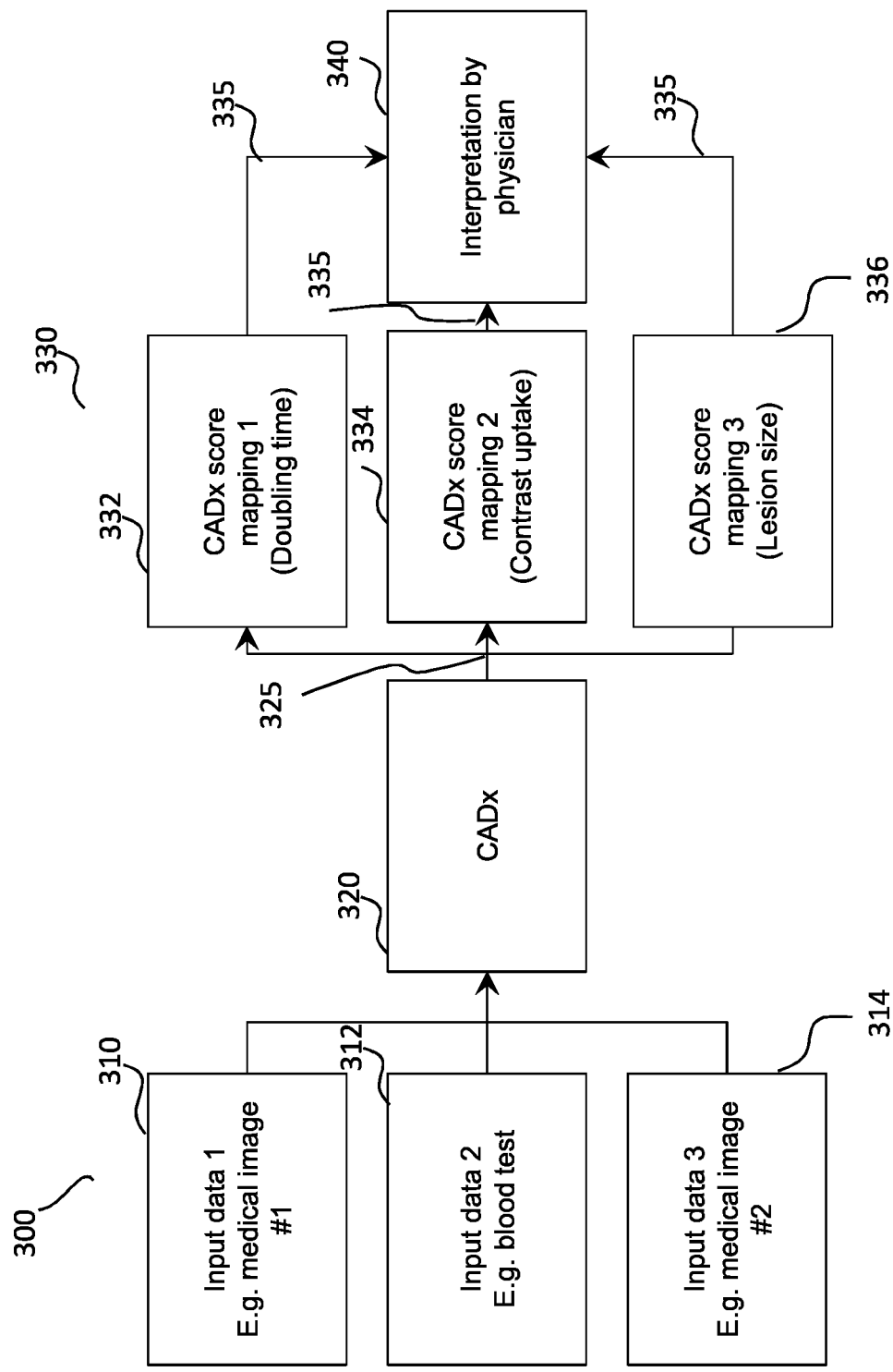
FIG. 3 illustrates a further example of a CADx based system that maps a raw CADx score to multiple clinically accepted scores, such as lesion doubling time, contrast uptake and lesion size, according to examples of the present invention.

Referring now to FIG. 3, a further example of a CADx based system 300 that maps a raw CADx score to one or multiple clinically accepted scores, referred to as risk adjusted virtual scores, according to a first approach is illustrated, where the mapping is directed to produce at least one risk adjusted virtual score, such as lesion doubling time, contrast uptake and lesion size, according to examples of the present invention.

Again, in this example, the CADx system 300 takes a number of inputs. In the illustrated example Data 1 is a medical image 310, Data 2 is a result of a blood test 312 and Data 3 is another medical image 314 (for example of another modality or taken at another time to Data 1). A CADx processing engine 320 takes such inputs and either automatically, or with some user-input, produces a score 325 that, say, indicates a risk of the condition or disease. For the purposes of illustration, let us assume that the output is a real number between '0' and '99', indicating the predicted absence or presence of the condition or disease respectively. In accordance with examples of the invention, this score 325 is then modified in CADx score mapping circuit 330 to at least one risk adjusted virtual score. The CADx score mapping circuit 330 may be implemented using logic gates in firmware in some example implementations, or in software. In some examples, the CADx score mapping circuit 330 modifies the standard CADx system output 325 by adding an additional step after the CADx processing engine 320 operation, in order to produce the at least one modified risk adjusted virtual score 335. According to examples of the invention, the CADx score mapping circuit 330 maps the raw CADx score 325 to a desired output scale. In this example, the CADx score mapping circuit 330 may encompass one or more of: a first CADx score mapping circuit that uses doubling time 332, a second CADx score mapping circuit that uses contrast uptake 334 and/or a third CADx score mapping circuit that uses lesion size 336. Again, the at least one modified risk adjusted virtual score 335 may then be interpreted by the radiologist or a physician at 340, with other clinical parameters, during a decision making by the radiologist or a physician.

This type of implementation has advantages in situations where the CADx system is already trained and validated and for practical purposes we do not wish to adapt it to the new scale. Another benefit of this approach is that the mapping step can be modified to suit user specific preferences without adapting the CADx system. In this manner, examples of the invention may allow a hospital or hospital system within a country, e.g. NHS England, to adapt the format of the output of the CADx system for their particular situation. For instance, it may be that the local or national guidelines for managing a given condition recommend measuring a size of a lesion, in order to stratify cancer patients, and hence the system would be able to map the CADx output to 'size'. In another country, the guidelines might recommend lesion volume.

Moreover, multiple such mappings can be produced in parallel as illustrated. This is a particularly useful feature of the system as it allows a single CADx processing circuit or algorithm to be used by different clinical specialties, e.g. surgeons, oncologists and radiologists, and can be adapted to different clinical contexts. For example, a surgeon may prefer to think about the size of a lesion, whereas an oncologist might be more familiar with, and prefer to consider, doubling time.

Mapping Function

In some examples of the invention, the CADx score mapping operation may be implemented in a number of ways but for many applications it is useful if the mapping exhibits smooth and monotonic properties. Smoothness is desired such that the output changes predictably with a change in the input. Monotonicity is beneficial so that the ordering of the raw CADx score is maintained.

One convenient technique to implement the CADx score mapping function is to use a piecewise polynomial function or spline to perform the mapping. Such functions typically have a small number of parameters and can be readily trained from example data using conventional optimisation algorithms such Least-squares fitting. In some other applications it is envisaged that it may be useful to truncate the output of the polynomial below and above certain values. An example of a suitable spline is a quadratic spline:

$$y(x) = ax^2 + b + c \quad [1]$$

Where: $x_0 \leq x < x_1$ is the domain of the mapping function.

In a quadratic spline there are three parameters that must be set. However, a number of such splines are typically used to define the overall mapping function. Hence, we may define 'k' splines across the whole domain of the mapping function, D=[A,B]. If the CADx output ranges between '0' and '99', as in the example above, the domain of the mapping function would be D=[0,99]

$$y_k(x) = a_k x^2 + b_k x + c_k \quad [2]$$

Where: $x_{k-1} \leq x_k < x_{k+1}$ spans D

Fitting the Mapping Function

In order to fit the mapping function it is necessary to provide a number of correspondences between the CADx scores and the desired output values. By a correspondence it is meant that for a number of values of the CADx score, a desired corresponding value for the output at least one risk adjusted virtual score must be determined. There must be sufficient examples to fit the mapping function; at least equal to the number of degrees of freedom of the mapping function. In practice, many more correspondences will be required to reliably fit the mapping function. In order to determine the mappings, in some examples equal values of clinical risk of disease between the two scores may be mapped to one another.

FIG. 4 illustrates one example of a mapping 400 of raw CADx data 410 to an equivalent size 420 and an equivalent PET SUV maximum value and associated risk, according to examples of the present invention.

Almost by definition, clinically accepted measurements are typically associated with condition or disease risk. For example, a 10 mm nodule, i.e. a nodule whose longest dimension is 10 mm, detected on a screening CT performed on a high-risk but asymptomatic patient population, has an approximately 2.5% chance of being cancerous. It is possible to also determine the same risk profile from a population using the CADx score using either the data used to train the system or a separate validation dataset. To do this, the proportion of benign and malignant lesions that achieved a particular score are counted. For example, a score of '45' on the same '0' to '99' scale described above corresponds to a 2.5% chance of disease within the dataset.

Therefore, one point correspondence is that a score of '45' can be represented as a having an equivalent long axis dimension of 10 mm. Given sufficient such correspondences, it is possible to apply and fit the mapping function to an equivalent size 420, as shown.

In other examples, and as a variation to the above, it may be beneficial to partition the score into ranges in order to perform the mapping. For instance, the ranges may encompass '0 to 9', '10 to 19', and so on.

Referring now to FIG. 5, a simplified graphical representation 500 of a mapping function 530 is illustrated to map CADx scores 520 to a risk adjusted virtual score in a form of equivalent size, according to examples of the present invention. In this example, the equivalent size is given in terms of an output equivalent lung nodule size 510.

Figure 6:
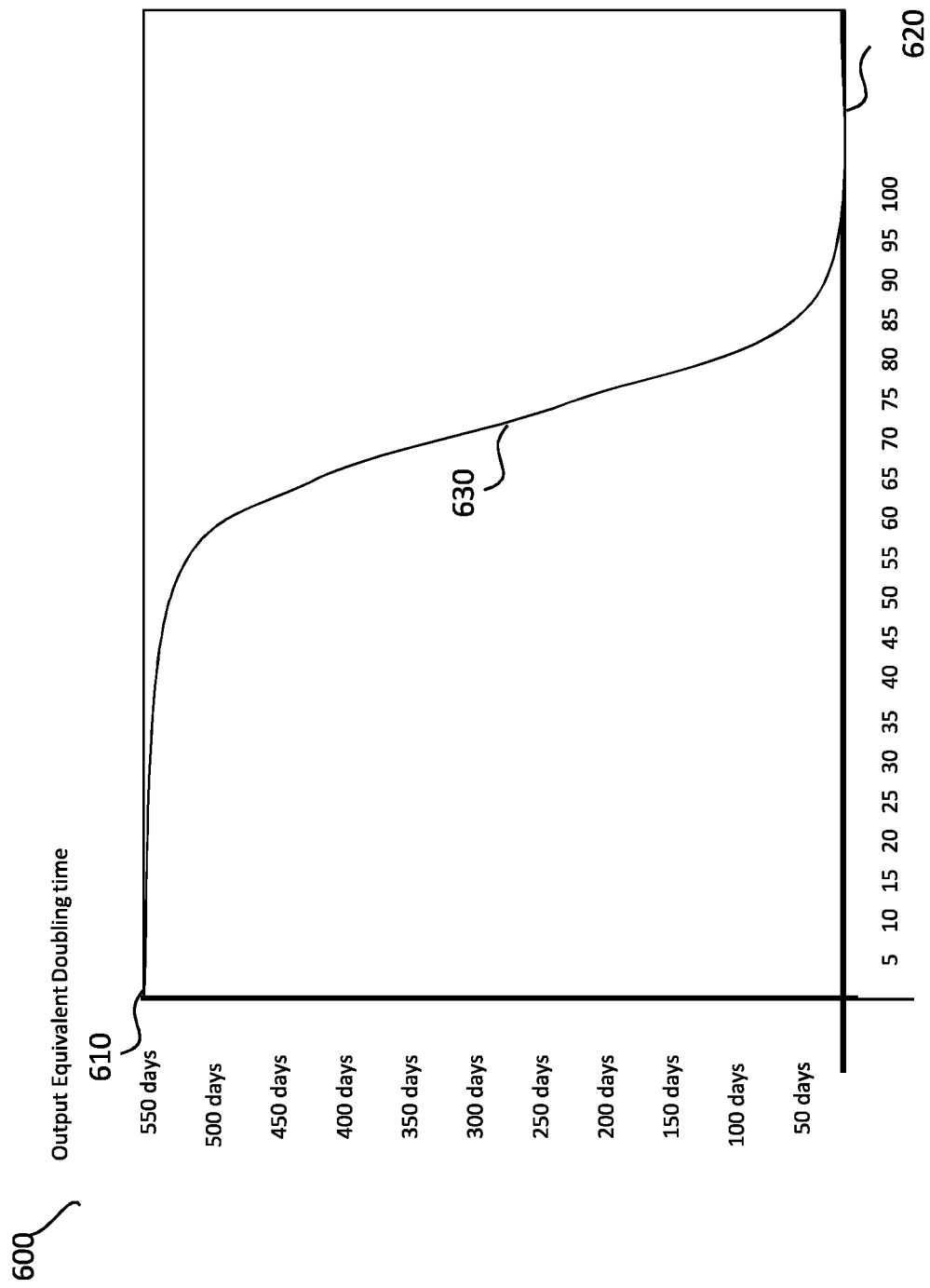
FIG. 6 illustrates a further graphical mapping function example, including mapping raw CADx score to equivalent doubling time, according to examples of the present invention.

Referring now to FIG. 6, a further simplified graphical representation 600 of a mapping function 630 is illustrated to map CADx scores 620 to a risk adjusted virtual score in a form of equivalent doubling time 610, according to examples of the present invention.

In some examples, the process of finding correspondences and fitting the mapping function for mapping a CADx score for, say, lung lesions to lesion size can proceed as follows. First, select a representative set of cases on which to run the CADx score. In some examples, this may be the dataset used to train and validate the CADx system or another independent dataset. Secondly, select a quantisation of the CADx score range, for example '0 to 9', '10 to 19', and so on up to '90 to 99' for a range implementation. Here, there is a trade-off between the degree of quantisation (or bin size) and ensuring that there is an adequate number of samples in each quantisation bin to represent the relationship between the CADx value and the empirical. Thirdly, the (empirical) risk of disease may be measured for each of a number of quantisation bins. In this third step, the measurement may be made by running the CADx on the dataset selected in the first step. Alternatively, the measurement may be made for each quantisation bin, by counting the number of cases for which the disease is present. The fraction of cases where the disease is present to the total number of cases may be assumed to represent the empirical risk of the condition or disease.

The result of the above operation will be a series of corresponding values between the CADx ranges and the empirical risk of disease and may be represented in a mapping table, as illustrated in Table 1.

TABLE 1

| | CADx range | | | | | | | | | |
|---|---|---|---|---|---|---|---|---|---|---|
| | 0-9 | 10-19 | 20-29 | 30-39 | 40-49 | 50-59 | 60-69 | 70-79 | 80-89 | 90-99 |
| Risk (%) | 0 | 0.1 | 2 | 5 | 30 | 60 | 80 | 90 | 97 | 100 |

In a fourth operation, and for each of the risk values, the process may determine a corresponding value for the desired output scale. For example, for mapping to nodule size, one could measure the diameter of each nodule in the training or validation set used to train the CADx system and to calculate the empirical risk as described in the second step. Here, the output may be of the form of mapping Table 2.

TABLE 2

| Nodule size(mm) | 6 | 7 | 8 | 9 | 20 | 25 | 27 | 28 | 29 | 30 |
|---|---|---|---|---|---|---|---|---|---|---|
| Risk (%) | 0 | 0.1 | 2 | 5 | 30 | 60 | 80 | 90 | 97 | 100 |

In a fifth operation, the corresponding values between the CADx score and the nodule sizes may be mapped by the mapping function using, say, standard curve fitting, such as a least-squares fit.

Figure 1:
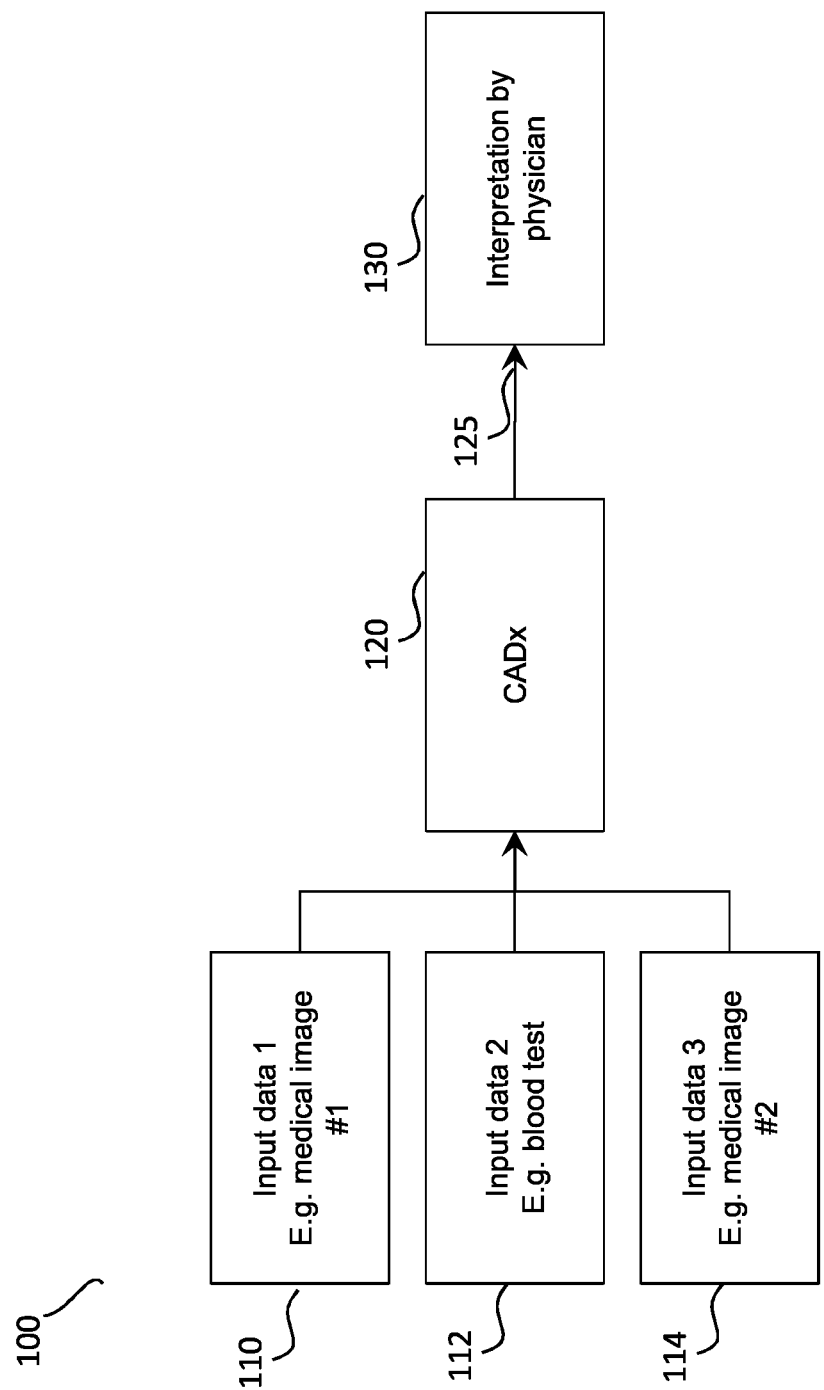
FIG. 1 illustrates a known block diagram of a conventional CADx system that takes one or more input datasets and produces a score as an indicator of the system's confidence of whether (or not) the dataset exhibits disease.

In some cases, it may not be possible to determine both scales on the same data. Therefore, in some examples, it is envisaged that the second and third steps may have to be performed on different datasets or derived from published results or models of risk. For example, the relationship between nodule size and risk of lung cancer is well studied and can be obtained in prior art publications, such as FIG. 1 shown in "Probability of Cancer in Pulmonary Nodules Detected on First Screening CT", McWilliams et al, N Engl J Med 2013; 369:910-919.

In some examples, it is envisaged that as an alternative to quantising the score, it may be more desirable to quantise the risk values into even ranges, or even adapt the quantisation of both the values and the risks.

Finally, in some cases it may not be possible to relate both the CADx scale and the desired output scale using the same risk values. For example, this may be due to a lack of data that covers particular risk values. Therefore, in some examples, it is envisaged that an interpolating function may be fitted to the tables generated in one or both of the second and third steps, and then the interpolating function may be used to determine the correspondences between the two scales.

In other examples, it is envisaged that there are many other alternatives to the above method for finding appropriate correspondences between the CADx score and the clinically accepted, risk adjusted virtual score. For instance, in other examples, it is envisaged that the system may also include other factors that affect patient cancer risk, such as smoking history, sex and age, etc., and combine this with the CADx score to produce an overall equivalent risk in order to perform the mapping.

Figure 7:
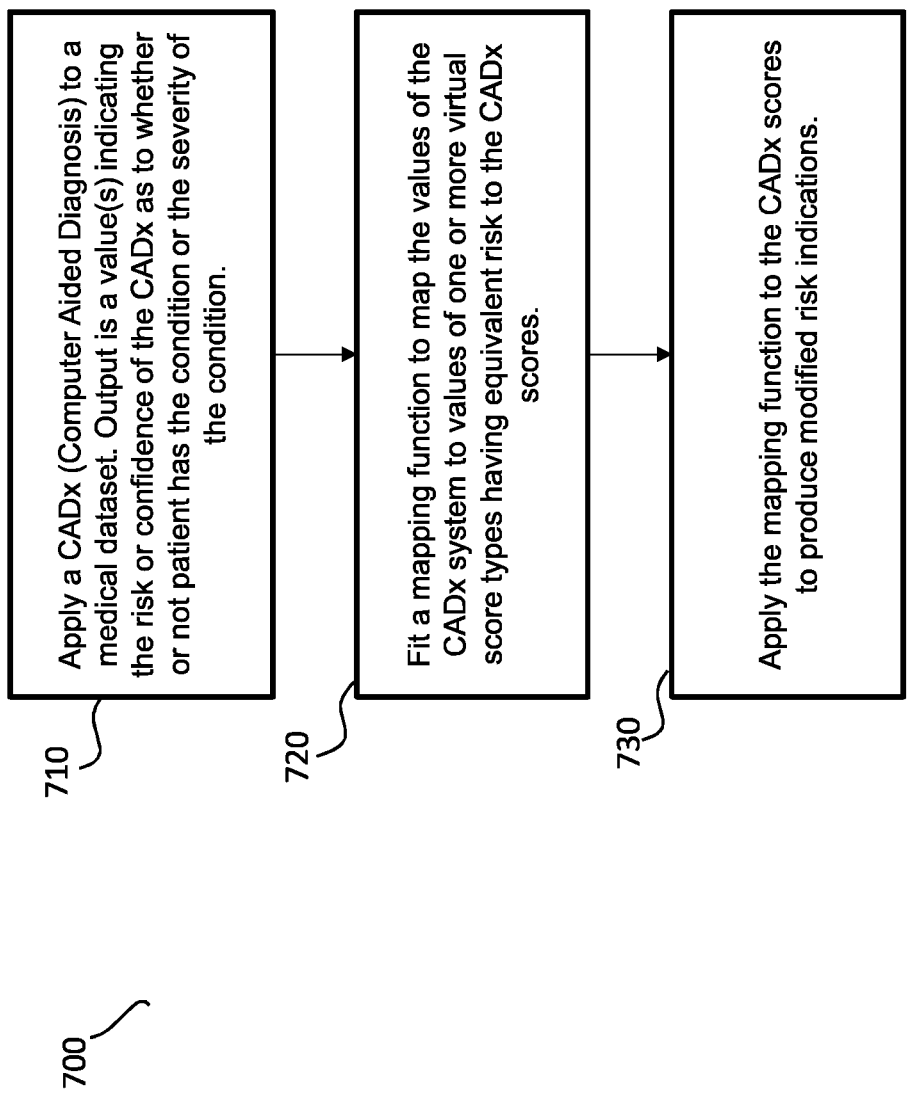
FIG. 7 illustrates an example of a flow diagram showing how the $1^{st}$ approach of any of FIGS. 2 to 6 may be trained, according to some examples of the present invention.

Referring now to FIG. 7, an example of a flow diagram 700 showing how the first approach may be trained is illustrated, according to some examples of the present invention. At 710, a known medical dataset is applied to a CADx system. The output is a value(s) indicating a risk or confidence of the CADx as to whether or not a patient has a particular condition or a severity of the condition. At 720, a mapping function to map the values of the CADx system to values of one or more risk adjusted virtual score types having equivalent risk to the CADx scores is applied. At 730, the mapping function is applied to the CADx scores to produce modified risk adjusted virtual score indications.

2nd Approach: Building into the CADx System

Figure 8:
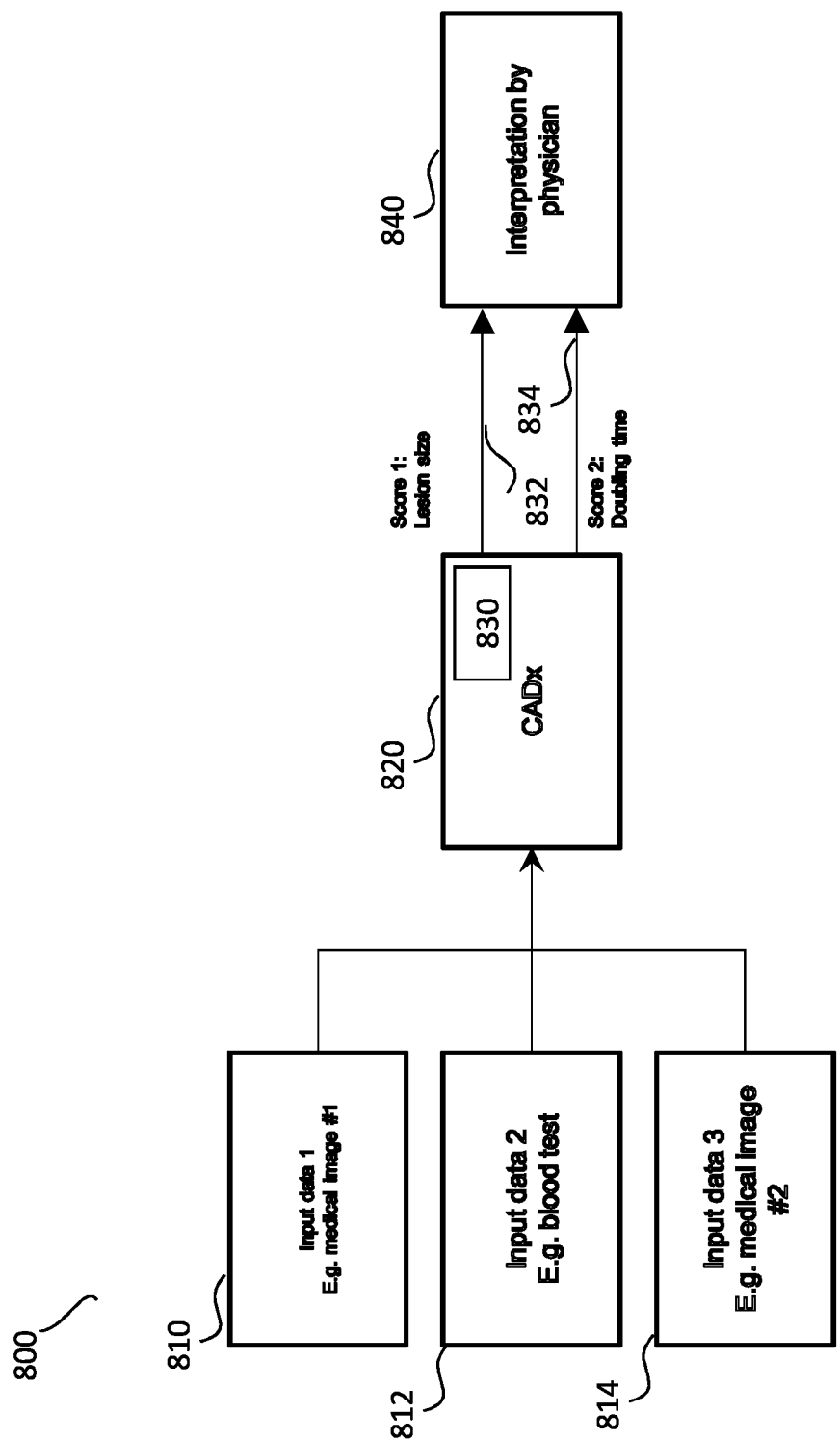
FIG. 8 illustrates an example of an alternative approach of a CADx system that performs a mapping of the raw CADx data to a clinically accepted score directly, without a separate and subsequent mapping step, according to some examples of the present invention.

Referring now to FIG. 8, an example of an alternative approach of a CADx system 800 is illustrated that performs a mapping of the raw CADx data to a clinically accepted risk adjusted virtual score directly, without a separate and subsequent mapping step, according to examples of the present invention. Again, in this example, the CADx system 800 may take a number of inputs, which in the illustrated example include Data 1 that is a medical image 810, Data 2 that is a result of a blood test 812 and Data 3 that is another medical image 814 (for example of another modality or taken at another time to Data 1). A CADx processing engine 820 takes such inputs and either automatically, or with some user-input, produces a score that, say, indicates a risk of the condition or disease. However, in this example, the CADx processing engine 820 has already modified the typical CADx score and outputs one or more modified risk adjusted virtual scores. Hence, the CADx processing engine 820 has been adapted to include the CADx score mapping circuit 830. The CADx score mapping circuit 830 may be implemented using logic gates in firmware in some example implementations or in software in other example implementations. In this example, the one or more modified output risk adjusted virtual scores may include a modified risk adjusted virtual score in a form of an equivalent lesion size 832 and/or a modified score in a form of a doubling time 834 with only two modified scores shown for illustration purposes only. The one or more modified risk adjusted virtual scores 832, 834 may then be interpreted by the radiologist or a physician at 840, with other clinical parameters, during a decision making by the radiologist or a physician.

As with the first approach, there are several ways in which a CADx score mapping circuit 830 can be implemented within the CADx processing engine 820. One convenient approach is to integrate within the CADx processing engine 820 a typically non-linear, regression algorithm that is trained to predict the desired output risk adjusted virtual scores directly. Regression algorithms are well-established methods in the field of machine learning and statistical estimation and are designed to produce, typically, continuous single or multi-dimensional numbers given their input. A basic regressor well known in the field is the linear regressor that produces an output number given a linear combination of it's inputs. In contrast to classification algorithms, which assign to the input data one of two or more classes, for example benign or malignant, regression algorithms can produce a real-valued number as their output. Therefore, in this example the classifier may be replaced with a regressor that is trained to predict the desired output scale or scale directly.

Figure 9:
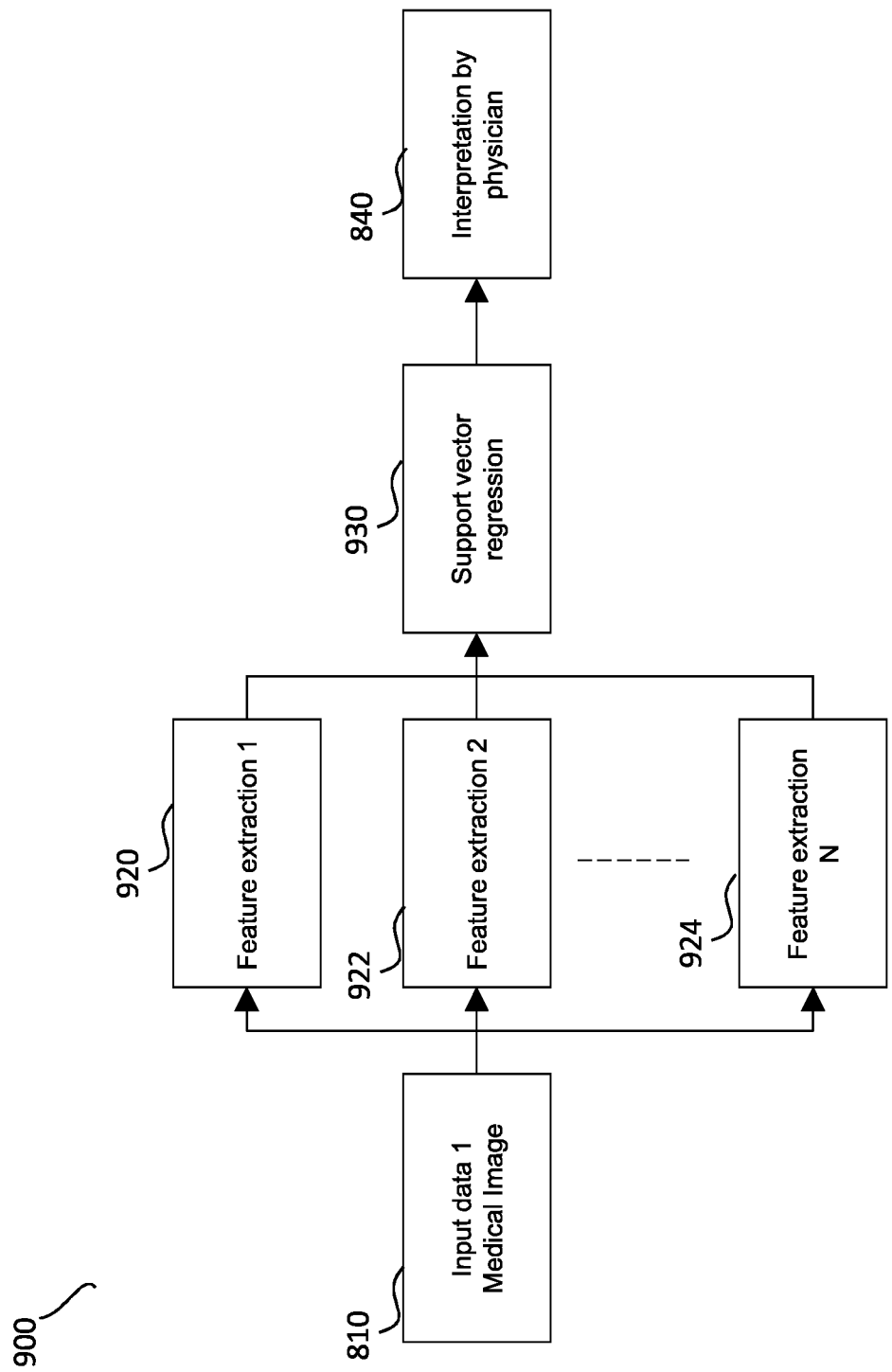
FIG. 9 illustrates a further exemplary implementation of the alternative approach of FIG. 8, where the CADx system uses a nonlinear regression algorithm to produce an output of the clinically accepted scores directly, according to examples of the present invention.

Referring now to FIG. 9, a further exemplary implementation of the alternative approach of FIG. 8, where the CADx system 900 uses a nonlinear regression algorithm to produce output of the clinically accepted risk adjusted virtual scores directly, is illustrated according to examples of the present invention. In this example, the CADx system 900 comprises a plurality of feature extraction circuits 920, 922, 924 that are arranged to extract features, e.g. a size of nodules, from the received medical image, say Data 1 that is a medical image 810. The extracted features are then provided to a regression circuit, which may be implemented in firmware using logic gates or as a software algorithm. There are many regression algorithms that may be suitable, including Random Forests, Support Vector Machines and Convolutional Neural Networks. The example of FIG. 9 utilizes a Support Vector Regression circuit 930, which may be implemented in firmware or software.

Figure 10:
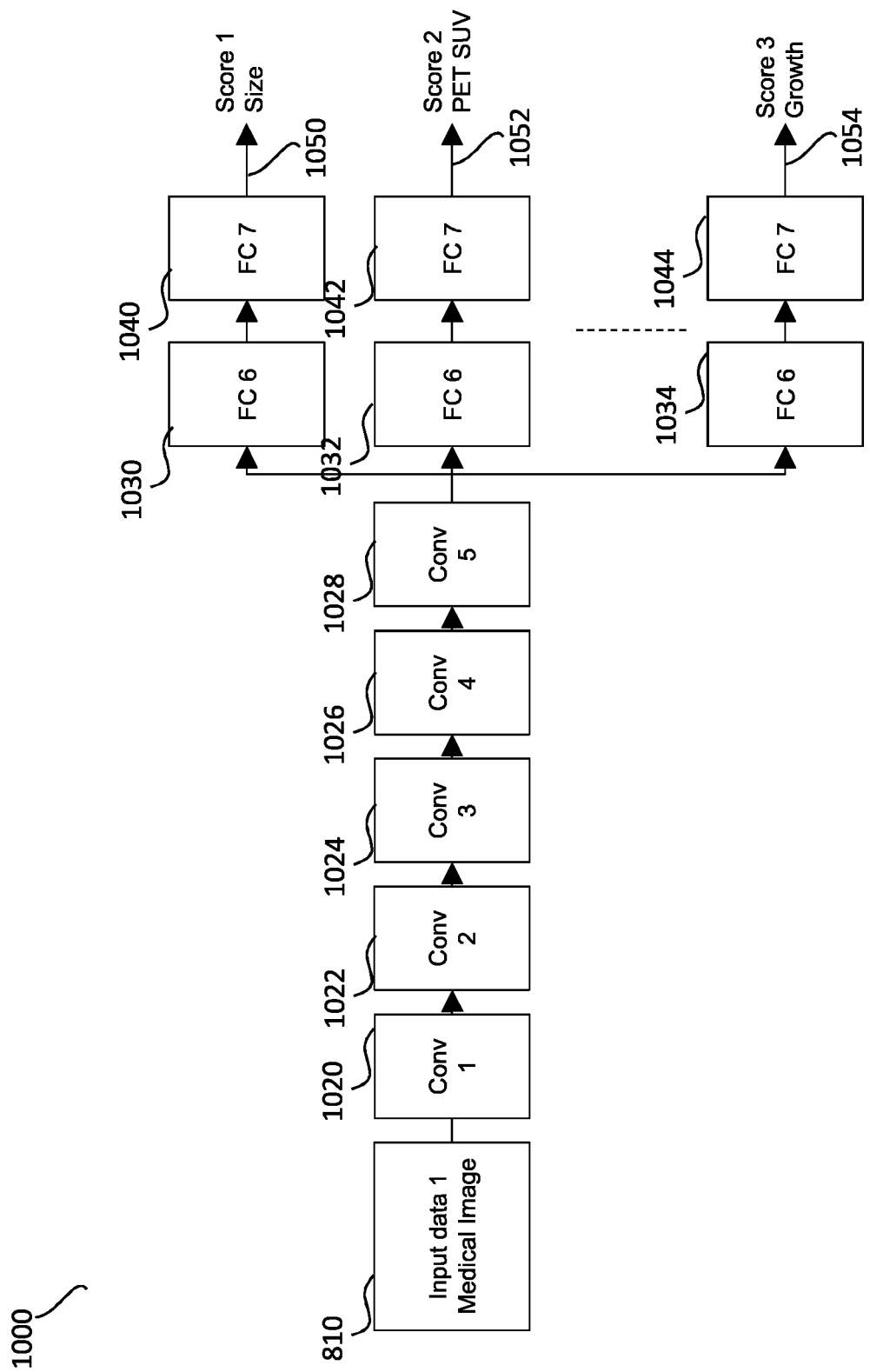
FIG. 10 illustrates a further alternative implementation of the alternative approach of FIG. 8, using a Convolutional Neural Network, configured to perform both the feature extraction and the regression, according to some examples of the present invention.

Referring now to FIG. 9, an alternative implementation of the alternative approach of FIG. 8 is illustrated, using a Convolutional Neural Network (CNN) 1000 as illustrated in FIG. 10, to perform both the feature extraction and the regression, according to examples of the present invention. Operation 1010 is the input data, in this case a medical image. Operations 1020 to 1028 represent the convolutional layers of the CNN. The implementation shown in FIG. 9 has several feature extraction steps that are typically hand selected features. In contrast, in a CNN the convolutional layers learn the features directly from the data and hence can be more optimally tuned to the application of interest. The convolutional layers are, in effect, a series of filters that are applied to the input where the parameters of the filters are learnt from the training data. The convolutional layers, or filters, might have different sizes in each of the layers, e.g. 3×3 pixels and might be 2D filters or 3D depending on the input image and the specific task of interest.

Five convolutional layers have been shown in this example implementation. However, in other examples, a greater or a fewer number may be used as is necessary for the application. Processing operations 1030 to 1044 show fully connected layers that have weights optimised to map the outputs of the convolutional layers to the desired output values. Unlike the convolutional layers that filter the input using convolution, these layers are typically simple weighted combinations of their inputs. The entire network can be optimised using conventional methods that can be applied to CNNs such as Back Propagation. The network described above is a conventional example that has been used successfully in the area of image classification and more details on its design and training are well-known in the literature e.g. "ImageNet Classification with Deep Convolutional Neural Networks" by Alex Krizhevsky, Ilya Sutskever and Geoffrey E. Hinton, Proceedings of Neural Information Processing Systems 2012.

Figure 11:
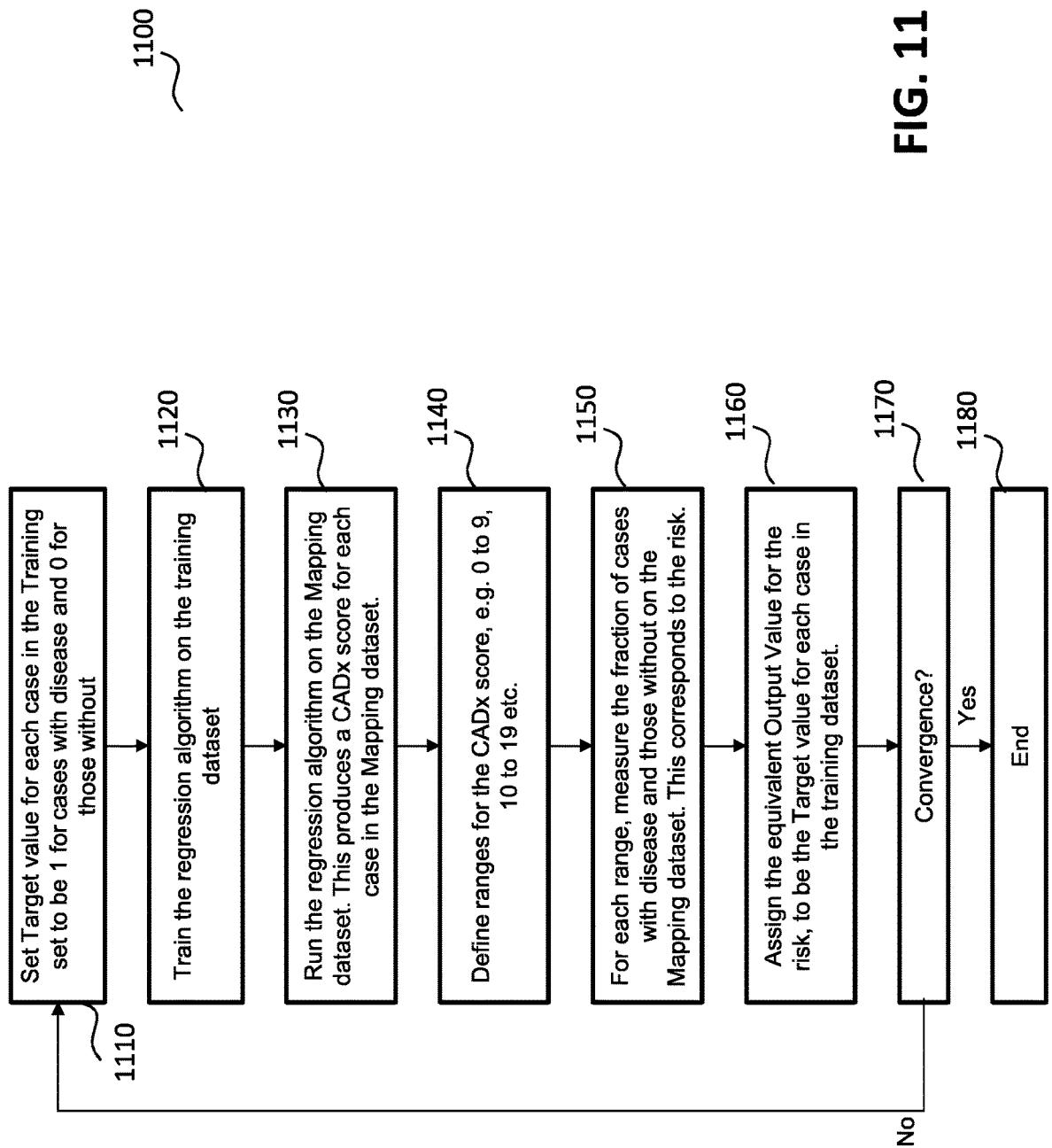
FIG. 11 illustrates an example of a flow diagram that shows how the alternative approach of FIGS. 8 to 10 may be trained, according to some examples of the present invention.

In order to train a regression algorithm, it is necessary to have desired output scores for each of the training examples that are used to train the system. Since, in some examples, the CADx system may not yet be trained, it is not possible to use the approach outlined in the 1st approach, namely the mapping of risk scores between the two scales at the outset of training. Instead, this process may be repeated periodically during a training of the CADx system. FIG. 11 illustrates an example of a flow diagram 1100 that shows how the alternative approach may be trained, according to some examples of the present invention. Unlike the first approach, the CADx system does not know a priori the risk associated with each training example.

At the outset, all Training set examples with disease are given a score of '1' and those without are scored '0', as in 1110; referred to as the Target value in 1110. The regressor is then trained to predict those scores at 1120. Next, the trained regression algorithm is run on the Training dataset or a separate Mapping dataset to produce a CADx score for each case in the Training or Mapping dataset respectively, at 1130. In some examples, this operation may include defining and allocating ranges to the mapped data, as in 1140. Once this operation is performed, for example for each range, it is possible to estimate the risks associated with each case in the Training or Mapping dataset. In the example shown in FIG. 11, in step 1150, the fraction of cases identified with the condition or disease, and those without the condition or disease, are measured on the Mapping dataset. This gives the risk of disease. The final step is to update the Target value for each case in the Training set to correspond to the value of the desired virtual score corresponding to the risk for that case. For example, if the desired risk adjusted virtual score is risk adjusted nodule size and a particular example in the Training has a risk of 5% as determined in step 1150, then using Table 2 we would set the Target value of that example to be 9 mm. This is performed for all cases in the Training set. The process is then repeated (with looping back to 1110) until convergence is reached at 1170, e.g. when the correspondences do not change very much or the risks associated with the training examples become stable. Once converged, the process ends at 1180.

In some examples, this iterative process may be performed after the regressor has been fully trained, as described above, or dispersed within the training of the regressor. For algorithms that train relatively quickly, such as Support Vector Machines as illustrated in FIG. 9, it is preferable to train the regressor fully before updating the mapping. For regression algorithms that take many hours or days to train, such as Convolutional Neural Networks as illustrated in FIG. 10, the updates should be performed during training iterations.

Thus, examples of the invention propose a technique that maps CADx scores to a clinically accepted risk adjusted virtual score. In particular, examples of the invention describe identifying correspondences between the CADx scores and one or more equivalent value(s) on a clinically accepted suitable scale. In some examples a use of a risk of condition or disease (or equivalent) to achieve the above correspondence and training a regressor to perform the mapping between the CADx scores and a clinically accepted scale may be performed. In this manner, examples of the invention provide a CADx system that is able to present its results on a scale that is clinically accepted and, hence, would be easier for clinical users to understand and adopt into their practice.

Although examples of the invention have been described with reference to a general regression circuit or algorithm, it is envisaged that the concepts described herein may be employed using polynomial or spline regression functions to perform the mapping. For example, in other examples, it is envisaged that the concepts may use least-squares fitting to fit the function.

Although examples of the invention have been described with reference to the system using a Support Vector Machine for classification, it is envisaged that the concepts described herein may use Random Forest, support vector machine or Convolutional Neural Network for the regression algorithm.

Although examples of the invention have been described with reference to an interpretation of medical images in a clinical setting e.g. in radiology, cardiology, oncology, it is envisaged that in other examples, the concepts described herein may be employed, say, within a clinical trial for a medical intervention e.g. drug, radiation therapy, etc.

Thus, examples of the invention describe a method and system for training a computer aided risk assessment to classify medical data related to at least one patient. The method (and components in the system) includes: assembling the medical data that comprises at least one medical image of the at least one patient, where the at least one medical image contains information associated with whether or not the at least one patient has a condition; analysing the assembled medical data by a CADx tool to obtain a first score output that indicates a value associated with the at least one patient having the condition; and fitting a mapping function, based on at least one other of the medical data, the first score output to at least one risk adjusted virtual score of at least one second score type having an equivalent risk to the first score, where the second score type provides a modified risk adjusted virtual indication. The output is a trained model that is used in the risk assessment system. In some examples, the at least one other medical data related to at least one patient may include training data that further comprises (in addition to medical images) at least one of: meta data (e.g. age, sex, smoking, etc.) and historical data (e.g. older scans, medical history . . . ).

In some examples, the modified risk adjusted virtual score may be of the same type as the original (non-mapped) first score type that provided the initial information. In some examples, the at least one risk adjusted (equivalent or) virtual score of at least one second score type may include an equivalent PET SUV. In some examples, the medical images may include chest computed tomography (CT) scans that show at least one pulmonary nodule. Expanding on these examples further, one novel approach to the management of pulmonary nodules is to perform a PET/CT scan of the patient and to use the measured PET SUV as a means to determine whether or not nodule is likely malignant or benign.

Therefore, we may train a CADx system to produce a score indicating the likelihood of nodule malignancy, e.g. a first score from 0 to 99, and map this to a virtual score corresponding to PET SUV. Or in the second approach, the CADx system can be trained directly to produce a virtual PET SUV score.

Once the system is trained, a clinical user can then use the trained model when making clinical decisions in managing such patients in the following manner. The user inputs a medical image into the trained system, along with related patient information such as age, smoking history and sex. In the first approach, the system then produces a first score that is then mapped to the risk adjusted virtual PET SUV score. The user can then interpret the output of the CADx system in the same way that a PET SUV value could be used, had it been performed. In the second approach, the CADx system directly outputs the risk adjusted virtual PET SUV score without the mapping step. This novel approach allows the output of a CADx system to be interpreted using a scale that many clinicians are familiar with and, hence, will be easier to adopt into clinical practice.

In some examples, the medical data related to at least one patient may include training data that further comprises (in addition to medical images) at least one of: meta data (e.g. age, sex, smoking, etc.) and historical data (e.g. older scans, medical history . . . ).

In some examples, the at least one risk adjusted (equivalent or) virtual score of at least one (modified) score type may include multiple risk adjusted virtual scores of multiple score types. In some examples, a fitting of a mapping function may include: identifying a range of possible values of a first (non-modified) score and allocating the first (non-modified) score into one of a plurality of sub-ranges, working out a risk of condition or disease for each of those plurality of sub-ranges, repeating the steps of separating and working for the risk adjusted virtual score, and deriving a mapping function that maps values of the first score to an equivalent risk of the risk adjusted virtual score. In some examples, the mapping may include using a piecewise or polynomial function or spline to perform the mapping. In some examples, the mapping may exhibit monotonic properties to enable the first score output value to be maintained in addition to the modified risk adjusted virtual score. In some examples, the mapping to a risk adjusted (equivalent or) virtual score may include deriving a mapping function that maps values of the first score to an equivalent risk of the risk adjusted virtual score on other published data. In some examples, the mapping may include converting a first score type to at least one risk adjusted (equivalent or) virtual score of at least one second score type using at least one of: an equivalent doubling time factor, an equivalent nodule size. In some examples, the mapping may include factoring in user specific preferences or more data of the at least one patient The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for training a computer aided risk assessment, the program code operable for training a computer aided risk assessment includes: assembling the medical data that comprises at least one medical image of the at least one patient, where the at least one medical image contains information associated with whether or not the at least one patient has a condition; analysing the assembled medical data by a CADx tool to obtain a first score output that indicates a value associated with the at least one patient having the condition; and fitting a mapping function, based on at least one other of the medical data, the first score output to at least one virtual score of at least one second score type having an equivalent risk to the first score, where the second score type provides a modified risk indication. The output is a trained model that is used in the risk assessment system.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The invention claimed is:

1. A Computer Aided Diagnosis, CADx, system comprising:
   at least one input configured to provide at least one input medical image;
   a CADx processing engine configured to receive and process the at least one input medical image and produce at least one CADx score; and
   a CADx score mapping circuit operably coupled to the CADx processing engine and configured to:
      map the at least one CADx score to a risk adjusted virtual score on a clinically accepted scale, wherein the risk adjusted virtual score provides a risk equivalence of malignancy based on training data in addition to the processed at least one medical image; and
generate an output of at least the risk adjusted virtual score associated with the processed at least one input medical image;
wherein the risk adjusted virtual score corresponds to a different equivalent risk of malignancy associated with a patient than the at least one CADx score that is based on the processed at least one input medical image.

2. The CADx, system of claim 1, wherein a first score that indicates a value associated with at least one patient having malignancy is at least one risk adjusted virtual score of at least one second score type having an equivalent risk to the first score, where the at least one second score type comprises at least one of:
a modified risk indication;
multiple virtual scores of multiple score types;
an equivalent Positron Emission Tomography, PET, standardised uptake value, SUV.

3. The CADx system of claim 2, wherein the CADx score mapping circuit is configured to convert the first score of a first score type to the at least one risk adjusted virtual score of the at least one second score type using at least one of: an equivalent doubling time factor, an equivalent nodule size.

4. The CADx system of claim 1, wherein the at least one medical image includes a chest-computed tomography, CT, scan that shows at least one pulmonary nodule.

5. The CADx system of claim 4, wherein a Positron Emission Tomography, PET, CT scan of a patient is performed and a measured PET standardised uptake value, SUV, output provides an input indication to the CADx system as to whether or not a nodule is malignant or benign, and the risk adjusted virtual score indicates a likelihood of nodule malignancy.

6. The CADx system of claim 5, wherein the measured PET SUV output is output either directly or is first mapped to a virtual PET SUV score that is output.

7. The CADx system of claim 1, wherein the at least one medical image includes both the at least one medical image and training data that comprises at least one of: meta data, historical data.

8. The CADx system of claim 1, wherein the CADx score mapping circuit is configured to exhibit monotonic properties that enable the output to include at least the risk adjusted virtual score associated with the processed at least one input medical image and the at least one CADx score.

9. The CADx system of claim 1, wherein the CADx score mapping circuit is configured to perform at least one from a group of:
use a Support Vector Machine for classification of mapping between the at least one CADx score and the risk adjusted virtual score;
include factoring in a mapping operation from at least one from a group of: user-specific preferences, more data associated with the patient.

10. A method of mapping a determined raw CADx score, the method comprising:
receiving and processing at least one input medical image by a CADx processing engine;
producing at least one CADx score;
mapping the at least one CADx score to a risk adjusted virtual score on a clinically accepted scale, wherein the risk adjusted virtual score provides a risk equivalence of malignancy based on training data in addition to the processed at least one medical image, wherein the risk adjusted virtual score corresponds to a different equivalent risk of malignancy associated with a patient than the at least one CADx score that is based on the processed at least one input medical image; and
generating an output of at least the risk adjusted virtual score associated with the processed at least one input medical image.

11. The method of mapping a determined raw CADx score of claim 10, wherein mapping further comprises:
identifying a range of possible values of a first non-modified score;
allocating the first non-modified score into one of a plurality of sub-ranges, dependent upon a determined risk of malignancy for each of the plurality of sub-ranges; and
repeating the steps of identifying, allocating and producing, and
deriving a mapping function that maps values of the first non-modified score to an equivalent risk of the virtual score.

12. A Computer Aided Diagnosis, CADx, system comprising:
at least one input configured to receive at least one input medical image of a patient; and
a CADx processing engine comprising a regressor circuit configured to process the received at least one input medical image;
wherein the regressor circuit is trained to generate a risk adjusted virtual score associated with the processed at least one input medical image on a clinically accepted scale, wherein the risk adjusted virtual score provides a risk equivalence of malignancy based on training data in addition to the processed at least one medical image and wherein the risk adjusted virtual score corresponds to a different equivalent risk of malignancy associated with the patient than a CADx score that is based on the processed at least one input medical image.

13. The CADx, system of claim 12, wherein the regressor circuit is configured to perform at least one of the following:
receive a training dataset and set a target value for each case in the training dataset that corresponds to an equivalent risk of the patient having malignancy;
perform a polynomial or spline regression or a piecewise function to perform the mapping between the at least one CADx score and one or more equivalent value(s) on a clinically accepted scale;
employ at least one from a group of: a Random Forest, Support Vector Machine, a Convolutional Neural Network.

14. A method of mapping a determined raw Computer Aided Diagnosis, CADx, score in a CADx system, the method comprising:
receiving and processing a plurality of input medical training images by a CADx processing engine;
allocating a score for each of the plurality of input medical training images, where the score comprises a range from a first score indicative of malignancy to a second score indicative of no malignancy;
iteratively training a regressor circuit coupled to the CADx processing engine to predict the score; and
generating a risk adjusted virtual score associated with each processed at least one input medical image on a clinically accepted scale, wherein the risk adjusted virtual score provides a risk equivalence of malignancy based on training data in addition to the processed at least one medical image and wherein the risk adjusted virtual score corresponds to a different equivalent risk of malignancy associated with a patient than a CADx score that is based on the processed at least one input medical image.

15. The method of mapping a determined raw CADx score of claim 14, wherein training a regressor circuit comprises:
   performing an iterative regression process on a mapping dataset; and
   generating a CADx score for each case in the mapping dataset.

16. The method of mapping a determined raw CADx score of claim 14, wherein training a regressor circuit comprises:
   defining and allocating ranges of the score to the mapped dataset.

17. The method of mapping a determined raw CADx score of claim 14, wherein training a regressor circuit further comprises:
   estimating a risk of malignancy associated with each input medical training image within a training population or measured on the mapping dataset;
   generating a risk adjusted virtual score associated with the respective input medical training image; and
   repeating a regression training operation until convergence is reached.

18. A Computer Aided Diagnosis, CADx, system comprising:
   at least one input configured to provide at least one input medical image; and
   a CADx processing engine configured to receive and process the at least one input medical image and produce at least one risk adjusted virtual score, on a clinically accepted scale, wherein the risk adjusted virtual score provides a risk equivalence of malignancy based on training data in addition to the processed at least one medical image and wherein the risk adjusted virtual score corresponds to a different equivalent risk of malignancy associated with a patient than a CADx score that is based on the processed at least one input medical image.

\* \* \* \* \*